US00RE40608E

(19) United States
(12) Reissued Patent
Glover et al.

(10) Patent Number: US RE40,608 E
(45) Date of Reissued Patent: Dec. 16, 2008

(54) ARRANGEMENT OF IVUS SYSTEM COMPONENTS INCLUDING REMOTE AND ADJACENT COMPONENTS

(75) Inventors: Richard Peter Glover, London (GB); Anthony David Stenning, Surrey (GB); Robert Julian Dickinson, London (GB)

(73) Assignee: Volcano Corporation, Rancho Cordova, CA (US)

(21) Appl. No.: 11/324,120

(22) PCT Filed: Dec. 22, 1999

(86) PCT No.: PCT/GB99/04343

§ 371 (c)(1),
(2), (4) Date: Jan. 15, 2002

(87) PCT Pub. No.: WO00/40156

PCT Pub. Date: Jul. 13, 2000

Related U.S. Patent Documents

Reissue of:
(64) Patent No.: 6,673,015
Issued: Jan. 6, 2004
Appl. No.: 09/869,637
Filed: Jan. 15, 2002

(30) Foreign Application Priority Data

Jan. 6, 1999 (GB) ..... 9900133

(51) Int. Cl.
*A61B 8/00* (2006.01)

(52) U.S. Cl. ..... 600/437
(58) Field of Classification Search ..... 600/407–473, 600/479, 481, 508; 128/899, 916; 601/2, 601/3; 607/122; 73/625, 626; 606/130, 159
See application file for complete search history.

(56) References Cited

U.S. PATENT DOCUMENTS

| | | | | |
|---|---|---|---|---|
| 4,625,731 A | | 12/1986 | Quedens et al. | |
| 5,465,724 A | | 11/1995 | Sliwa et al. | |
| 5,544,654 A | | 8/1996 | Murphy et al. | |
| 5,687,717 A | | 11/1997 | Halpern et al. | |
| 5,730,146 A | | 3/1998 | Itil et al. | |
| 5,765,565 A | | 6/1998 | Adair | |
| 6,017,307 A | * | 1/2000 | Raines | 600/300 |
| 6,059,731 A | | 5/2000 | Seward et al. | |
| 6,142,946 A | * | 11/2000 | Hwang et al. | 600/459 |

FOREIGN PATENT DOCUMENTS

| | | | |
|---|---|---|---|
| DE | 43 16 643 A | | 12/1993 |
| DE | 19 53 46 63 A | | 3/1997 |
| JP | 4316643 A1 | * | 12/1993 |

OTHER PUBLICATIONS

Search Report in corresponding GB Appln No. 9900133.1, date Mar. 10, 2000.

* cited by examiner

*Primary Examiner*—Eric F. Winakur
*Assistant Examiner*—Lawrence N Laryea
(74) *Attorney, Agent, or Firm*—Leydig, Voit & Mayer Ltd

(57) ABSTRACT

In an IVUS system, units are located outside or remote from the patient except for the display monitor (12), the catheter interface module (4) and the catheter (3) which are located adjacent the patient together with a control arrangement (13) to enable the said units to be remotely controlled from a position adjacent the patient.

20 Claims, 3 Drawing Sheets

ARRANGEMENT OF IVUS SYSTEM COMPONENTS INCLUDING REMOTE AND ADJACENT COMPONENTS

Matter enclosed in heavy brackets [ ] appears in the original patent but forms no part of this reissue specification; matter printed in italics indicates the additions made by reissue.

INTRODUCTION TO THE INVENTION

The present invention relates to ultrasonic visualisation systems and more particularly to systems of the kind to which our United Kingdom patent 2,233,094 and U.S. Pat. No. 5,257,629 relate. Such systems will hereinafter be referred to as intravascular ultrasound systems or IVUS.

Such systems include various units such as a cathode ray tube monitor, an ultrasound processing unit, a power distribution unit, and possibly a video recorder (VCR), together with a video printer as well as the catheter to be inserted into the patent and a catheter interface module linking the catheter to the other units referred to.

It has been proposed to mount the above types of unit in a cart or trolley that can be maneuvered into an appropriate position within the catheter laboratory or other relevant environment.

In such an arrangement the catheter and its associated catheter-interface-module (CIM), are not mounted on the cart or trolley because the catheter is to be inserted into the patient and the CIM would typically rest on or near the patient.

The floor area adjacent to the patient is at a premium because of the need to accommodate the medical team close to the patient. As a result, it is usually necessary to locate the cart or trolley some distance from the patient which in turn means that the display monitor has to have a reasonably large screen in order for the displayed image to be clearly visible to the clinician.

SUMMARY OF THE INVENTION

The present invention is concerned with the physical location of such units of the system in order to improve the operating environment for the medical team.

According to one aspect of the present invention in an IVUS system the said units are located outside or remote from the patient except for the display monitor, the CIM and the catheter which are located adjacent the patient together with a control arrangement to enable the said units to be remotely controlled from a position adjacent the patient.

According to a first aspect of the present invention, the display monitor comprises a flat screen monitor such as a liquid crystal display.

Because the monitor can now be located much nearer to the patient it can be made much smaller and still provide the clinician with a clearly visible image.

According to a second aspect of the present invention, the control arrangement incorporates means to enable control instructions to be given by voice and incorporates voice recognition manes for accepting and implementing those instructions.

According to a third aspect of the present invention, an IVUS system is embedded in a conventional ultrasound system which employs a transducer placed externally of the patient so that units of the conventional ultrasound system can also be employed in the IVUS system thus avoiding the duplication of those units. In other words, certain units are common to both the conventional ultrasound system and the IVUS system.

According to a fourth aspect of the present invention, the IVUS system is embedded in an existing X-ray system, again so that units common to both systems can be shared.

According to a fifth aspect of the present invention, the control arrangement includes an infrared remote control device to enable control instructions to be given from a position adjacent the patient to the remotely located units.

According to a sixth aspect of the present invention, the monitor is mounted on the CIM unit.

DETAILED DESCRIPTION OF THE PREFERRED EMBODIMENTS

Figure 1:
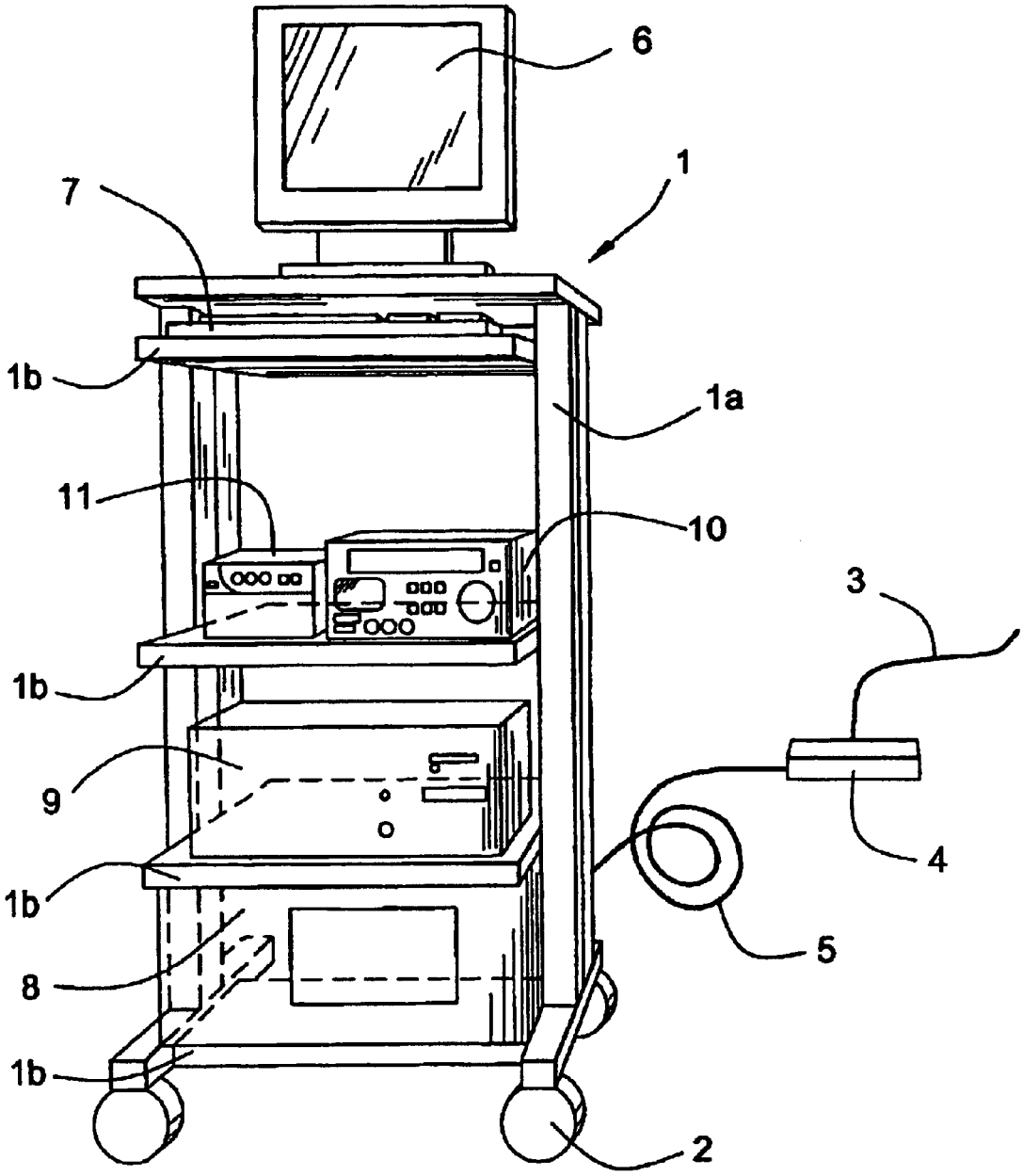
FIG. 1 (PRIOR ART)
FIG. 1 is a perspective view of a known mobile cart or trolley of the kind already described.

A cart or trolley 1 is provided with casters 2 by which it can be maneuvered within a catheter laboratory or other relevant environment.

A catheter 3 for insertion into a patient, is connected to a catheter interface module 4 which in turn is connected by a cable 5 to the various units carried by the trolley 1.

These units typically comprise a cathode ray tube monitor 6 mounted on the top of the cart or trolley 1, a keyboard and trackball 7 for controlling the display on the monitor, a power distribution unit 8, an ultrasound processing unit 9 (which could be a personal computer), a video recorder (VCR) 10 and an associated video printer 11.

The cart or trolley 1 typically comprises a framework 1a and a number of shelves 1b.

As discussed earlier, the cart or trolley arrangement shown in FIG. 1 would be located within the catheter laboratory or other relevant environment as close as possible to the patient without taking up floor space which would be needed by the medical team adjacent the patient. As a result the size of the screen of the monitor 6 has to be relatively large in order to provide a clear and visible display to the clinician.

The essence of the present invention is the elimination of the trolley or cart 1 and the positioning at a remote location of most of the units normally carried by the trolley as shown in FIG. 1.

The only units which would be located adjacent the patient are the CIM 4, a display screen 12 mounted on the CIM 4, and a control panel 13 by which the various units making up the system can be controlled. The catheter 3 is of course close to the patient as it has to be inserted into the patient.

Because the screen of the monitor 12 is close to the patient and therefore to the clinician, that screen can be much smaller than the screen of the known arrangement of FIG. 1.

In fact, instead of comprising a cathode ray tube display, the monitor 12 could comprise a flat liquid crystal display or other type of flat screen display.

The control panel can be through a simple local control such as a trackball, joy stick or similar pointing device, combined with Windows based software, and be very small. Alternatively, the control can be mounted with other control devices such as an X-ray gantry and bed controls.

To make control of the system easier a remote handset could be used. This could operate through an infrared link (or similar wireless communication), to the bedside unit, or directly with the processing hardware as an alternative where the room configuration demands it. This handset could provide all the control required to run the IVUS system such as adjusting gain, image magnification etc, and replaces the slides and buttons of a normal IVUS system.

According to a further aspect of the present invention, the system control could make use of voice-recognition technology. Here the handset could be employed with links to the processing hardware. System generated speech could be employed to allow interaction between operator and system that would make the need for close observation of the display less important. Recognition of key words could allow any function to be activated etc. Text entry could be managed in a similar way.

The advantages of the arrangements according to the present invention, so far described, is that the processing hardware is now free of display and interface devices such as a keyboard, and can be made small enough to be positioned in a convenient place such as underneath the patient's bed.

Overhead monitors in the room can be used as an alternative or additional display.

Figure 3:
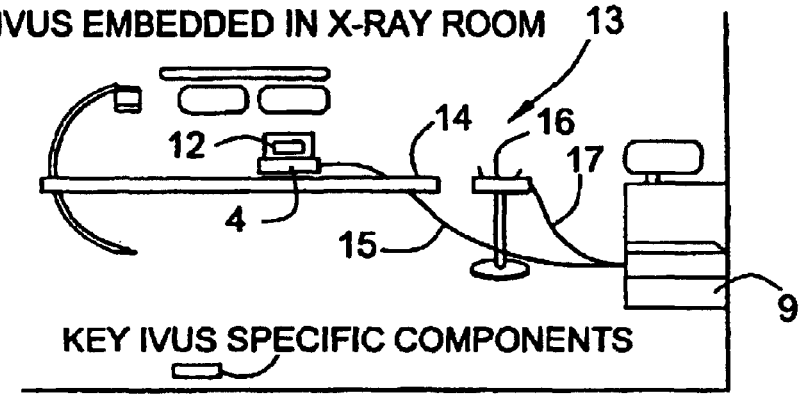
FIG. 3 is a diagrammatic representation of an IVUS embedded in a standard X-ray room according to the present invention.

Alternatively, it can be housed with the X-ray electronics in the X-ray control room, an arrangement of this kind being shown in FIG. 3. The IVUS system can then make use of the standard peripherals such as printers and digital or video recorders already provided in the X-ray room. The processing hardware in the control room can also be provided with a parallel set of operating controls to enable operation from outside the catheter lab, by a suitable operator, and a patient's details can be entered from this control room.

Figure 2:
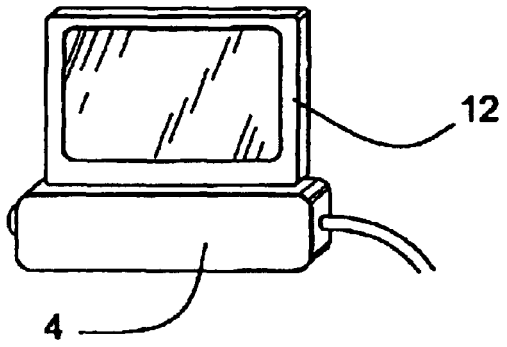
FIG. 2 is a perspective view of a combined display and catheter-interface-module according to the present invention.

Referring to FIG. 3, a patient's bed is indicated at 14 with the arrangement shown in FIG. 2 adjacent the bed.

The CIM 4 is connected to the IVUS computer 9 through an electrical connection 15 and a remote control joystick-type arrangement 16 is also connected to the computer 9 through an electrical connection 17.

All the other units required to make the IVUS system operative are already incorporated in the known standard X-ray equipment.

The data processing performed in an IVUS system consists of a series of discrete operations arranged in what is known as a pipeline. This means that the output of one process is the input of the next process. These processes can be arranged as separate modules, such as individual circuit cards, that are linked through a standard interface. An example of this is a set of dedicated cards that plug in to a peripheral component interconnect (PCI), computer bus. It then becomes possible to utilise commonly available standard cards or components to perform some of the non-IVUS specific processing such as data storage and archive, display drivers and power supplies. In this example the processing could be performed in a standard personal computer.

Figure 4:
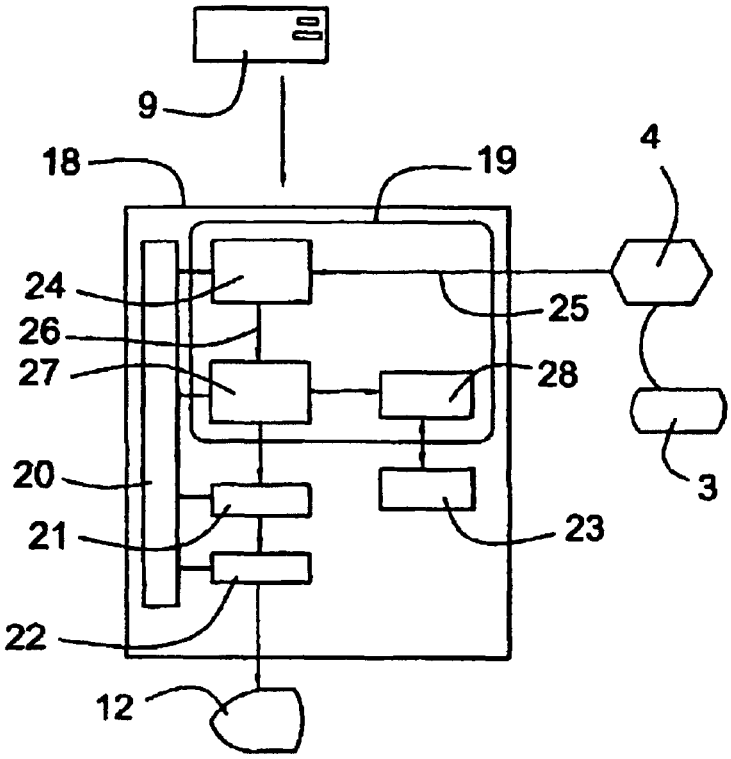
FIG. 4 is a block diagram showing an IVUS embedded in a personal computer according to the present invention.

FIG. 4 illustrates an embodiment of the IVUS processing modules.

In FIG. 4 those items which are equivalent to items already described with reference to FIGS. 1 to 3 have the same reference numerals.

In FIG. 4 the overall personal computer arrangement is illustrated within the box 18.

Contained within the box 18 are the modules which are specific to the IVUS system and these are contained within the smaller box 19.

The modules which are within the box 18 but not within the smaller box 19 are those which could be standard items in many known imaging systems such as external ultrasound imaging systems.

These common units include a personal computer bus 20, a scan conversion module 21, a graphics card 22 and a unit such as a CD-ROM for storing data and archiving media 23. The modules which are specific to the IVUS system in box 19 comprise an analogue to digital converter module 24 which takes an analogue input 25 from the catheter-interface-module 4.

The output from the ADC 24 is raw digital data 26, which is input to a digital signal processing card 27 which is concerned with focusing and beam forming.

The card 27 is interconnected with a data store 28 which itself is also interconnected with the module 23.

With this arrangement one module 24 performs all of the data-capture operations and also undertakes the interface with the catheter-interface-module 4.

A second module 27 undertakes the intensive numerical calculations required to focus the received data signals. This is typically a focusing and noise reduction operation.

The outputs from 27 would typically be digital and have a much lower bandwidth than the input to this module. This output consists of focused A-scans which can be temporarily stored in a local disk 28, and archived suitable removable media 23. Alternatively, the output of module 21 can be stored and archived using a similar arrangement.

The module 21 performs scan conversion of the digital data to allow representation of it on raster-scanned display devices such as conventional computer monitors or video screens.

This operation is similar to the interpolation and zoom functions found in many imaging modalities.

The IVUS modality can therefore be incorporated into another imaging modality by utilising the following components:

(i) catheter-interface-module arid display 4, 12

(ii) control device 13

(iii) data acquisition module 24

(iv) digital processing module 27

(v) it may be necessary to also incorporate a scan conversion card 21 into the box 19.

In a further aspect of the present invention, and in particular of the processing hardware, the digital processing function could be incorporated into the IVUS data acquisition module.

This would employ custom digital chip design techniques resulting ASICs or FPGAs to embed the processing operation. An example of which is synthetic aperture processing.

The system could then consist of a single module that can be incorporated into another imaging modality such as conventional external ultrasound. The same technique could also be used in standard computer systems to provide IVUS.

Figure 5:
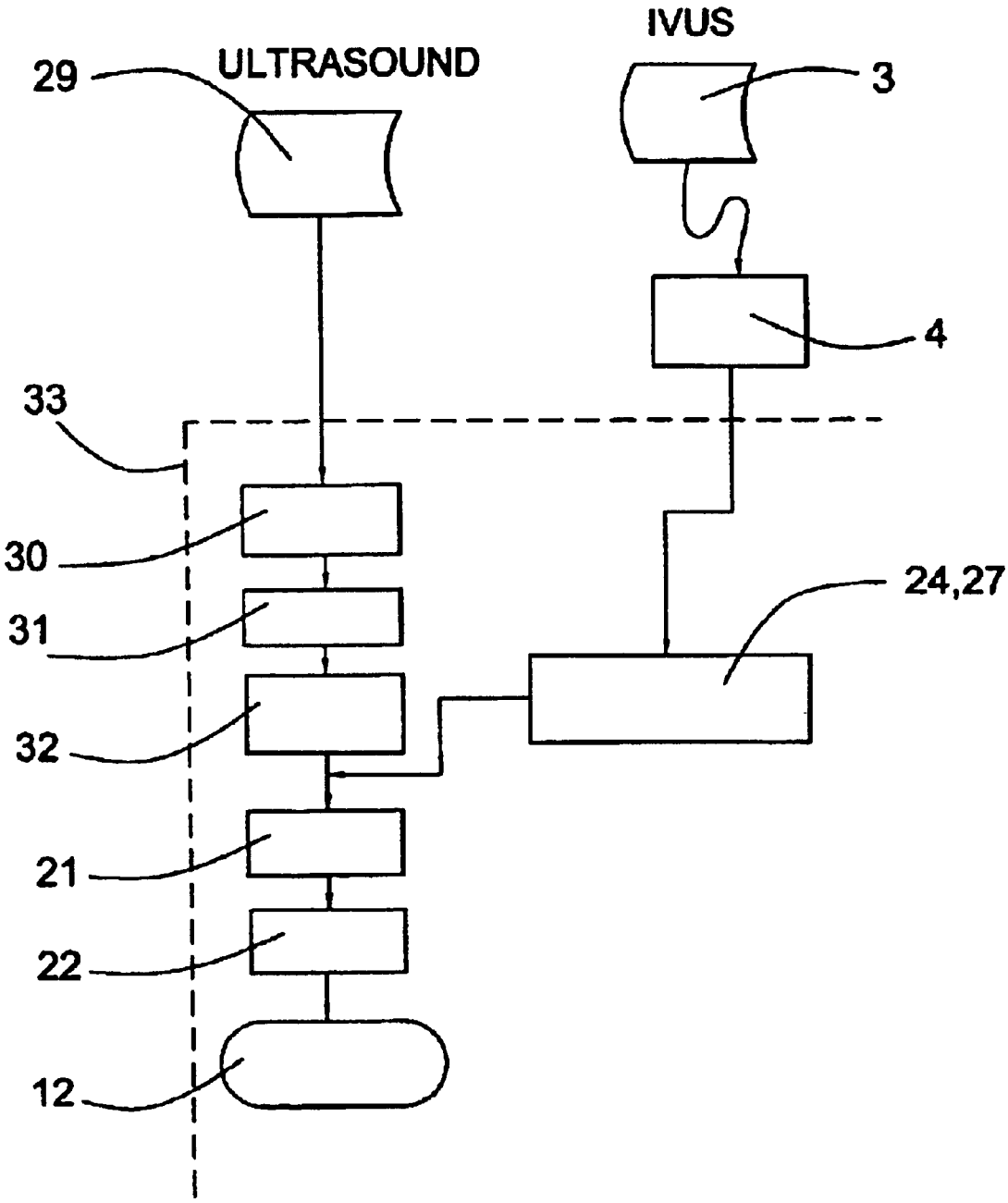
FIG. 5 is a block diagram showing a single board IVUS embedded in an ultrasound system.

FIG. 5 illustrates an embodiment of such an arrangement. Where those units or components which correspond with ones already described and illustrated have the same reference numerals.

A conventional external ultrasound has a transducer 29 the output signal of which inputs to a transmit/receive module 30 which in turn inputs to an analogue to digital converter (ADC) 31, which in turn inputs to a digital beam former 32. In parallel the IVUS system takes the signals from the transducer at the distal end of the catheter 3, passes them through the catheter-interface-module 4 and the combined ADC and focusing/beam forming module 24–27, the output of which is common with the output from the digital beam former 32, both of which input into the scan converter 21 followed by the graphics memory 22 and the display 12.

The dotted line 33 indicates the single board comprising essentially an IVUS system embedded in a known conventional ultrasound system.

What is claimed is:

1. An IVUS system comprising:

a) a catheter having an ultrasonic transducer array mounted at least near a distal end thereof;

b) a catheter interface module connected to a proximal end of the catheter;

c) a display monitor;

d) a control device for controlling the system;

e) a signal processing data entry and data storage device for processing and storing data derived from energizing the ultrasonic transducer array to output a signal to the display monitor in order to display an image of an interior of a patient's body; and f) a bed for supporting a patient, wherein the catheter interface module, the display monitor and the control device are located adjacent to the bed such as to be easily viewed and operated respectively by a clinician, and wherein the signal processing data entry and storage device is located remotely from the bed at a sufficient distance to enable a clear space around the bed for occupation by a medical team so that the medical team can be adjacent to the patient, and wherein the control device includes a wireless remote control device to enable control instructions to be given from a position adjacent the patient to remotely located units.

2. An IVUS system as claimed in claim 1 in which at least one of the following is located remotely from the bed:

(i) a power distribution unit;

(ii) a video recorder; and (iii) a video printer.

3. An IVUS system as claimed in claim 1 in which the display monitor comprises a flat screen monitor.

4. An IVUS system as claimed in claim 1 in which the control device incorporates a device to enable control instructions to be given by voice and incorporates a voice recognition device for accepting and implementing those instructions.

5. An IVUS system as claimed in claim 1 wherein the IVUS system is embedded in a conventional ultrasound system employing a transducer placed externally of the patient, so that units common to the IVUS system and the conventional ultrasound system can be shared.

6. An IVUS system as claimed in claim 1 wherein the IVUS system is embedded in an X-ray system, so that units common to the IVUS system and the X-ray system can be shared.

7. An IVUS system as claimed in claim 1 in which the wireless control device comprises an infra-red remote control device.

8. An IVUS system as claimed in claim 1 in which the display monitor is mounted on the catheter interface module.

9. A method of arranging components of an IVS system, the method comprising:

providing an IVUS system having:

a catheter having an ultrasonic transducer array mounted at least near a distal end thereof, a catheter interface module connected to a proximal end of the catheter;

a display monitor, a control device for controlling the system, a signal processing data entry and data storage device for processing an storing data derived from energizing the ultrasonic transducer array to output a signal to the display monitor in order to display an image of an interior of a patient's body, and a bed for supporting a patient;

locating the catheter interface module, the display monitor and the control device adjacent that bed such as to be easily viewed and operated respectively by a clinician; and locating the signal processing data entry and data storage device remotely from the bed at a sufficient distance to enable a clear space around the bed for occupation by a medical team so that the team can be adjacent the patient.

10. A method as claimed in claim 9, comprising the step of locating at least one of the following at a position remote from the bed:

(i) a power distribution unit;

(ii) a video recorder; and (iii) a video printer.

*11. An IVUS system comprising:*

*a) a catheter having an ultrasonic transducer mounted at least near a distal end thereof;*

*b) a catheter interface module connected to a proximal end of the catheter;*

*c) a display monitor;*

*d) a control device for controlling the system;*

*e) a signal processing data entry and data storage device for processing and storing data derived from energizing the ultrasonic transducer to output a signal to the display monitor in order to display an image of an interior of a patient's body; and*

*f) a bed for supporting a patient, wherein the catheter interface module, the display monitor and the control device are located adjacent to the bed such as to be easily viewed and operated respectively by a clinician, and*

*wherein the signal processing data entry and storage device is located remotely from the bed at a sufficient distance to enable a clear space around the bed for occupation by a medical team so that the medical team can be adjacent to the patent, and wherein the control device includes a wireless remote control device to enable control instructions to be given from a position adjacent the patient to remotely located units.*

*12. An IVUS system as claimed in claim 11 in which at least one of the following is located remotely from the bed:*

*(i) a power distribution unit;*

*(ii) a video recorder; and*

*(iii) a video printer.*

*13. An IVUS system as claimed in claim 11 in which the display monitor comprises a flat screen monitor.*

*14. An IVUS system as claimed in claim 11 in which the control device incorporates a device to enable control*

*instructions to be given by voice and incorporates a voice recognition device for accepting and implementing those instructions.*

*15. An IVUS system as claimed in claim 11 wherein the IVUS system is embedded in a conventional ultrasound system employing a transducer placed externally of the patient, so that units common to the IVUS system and the conventional ultrasound system can be shared.*

*16. An IVUS system as claimed in claim 11 wherein the IVUS system is embedded in an X-ray system, so that units common to the IVUS system and the X-ray system can be shared.*

*17. An IVUS system as claimed in claim 11 in which the wireless control device comprises an infra-red remote control device.*

*18. An IVUS system as claimed in claim 11 in which the display monitor is mounted on the catheter interface module.*

*19. A method of arranging components of an IVS system, the method comprising:*

*providing an IVUS system having:*

*a catheter having an ultrasonic transducer mounted at least near a distal end thereof,*

*a catheter interface module connected to a proximal end of the catheter;*

*a display monitor,*

*a control device for controlling the system,*

*a signal processing data entry and data storage device for processing an storing data derived from energizing the ultrasonic transducer to output a signal to the display monitor in order to display an image of an interior of a patient's body, and*

*a bed for supporting a patient;*

*locating the catheter interface module, the display monitor and the control device adjacent the bed such as to be easily viewed and operated respectively by a clinician; and*

*locating the signal processing data entry and data storage device remotely from the bed at a sufficient distance to enable a clear space around the bed for occupation by a medical team so that the team can be adjacent the patient.*

*20. A method as claimed in claim 19, comprising the step of locating at least one of the following at a position remote from the bed:*

*(i) a power distribution unit;*

*(ii) a video recorder; and*

*(iii) a video printer.*

* * * * *